United States Patent [19]

Swered et al.

[11] 3,962,456

[45] June 8, 1976

[54] SLIME CONTROL COMPOSITIONS AND THEIR USE

[75] Inventors: Paul Swered, Philadelphia; Bernard F. Shema, Glenside, both of Pa.

[73] Assignee: Betz Laboratories, Inc., Trevose, Pa.

[22] Filed: Aug. 11, 1975

[21] Appl. No.: 603,899

Related U.S. Application Data

[63] Continuation-in-part of Ser. No. 545,676, Jan. 30, 1975, abandoned.

[52] U.S. Cl................................ 424/298; 71/67; 162/161; 210/64; 424/327; 424/349
[51] Int. Cl.$^2$........................................ A01N 9/20
[58] Field of Search..................... 424/349, 298, 327

[56] References Cited
UNITED STATES PATENTS

| | | | |
|---|---|---|---|
| 3,733,419 | 5/1973 | Gutman | 424/327 |
| 3,827,873 | 8/1974 | Shema et al. | 424/329 X |

Primary Examiner—Leonard Schenkman
Attorney, Agent, or Firm—Alexander D. Ricci; Steven H. Markowitz

[57] ABSTRACT

The present invention relates to certain processes and compositions useful for inhibiting the growth of slime in water and, in particular, water used for industrial purposes; for example, in the manufacture of paper, in cooling water systems and in effluent water treatment. The novel processes and compositions of the present invention are processes or mixtures which show unexpected synergistic activity against microorganisms, including bacteria, fungi, and algae, which produce slime in aqueous systems or bodies which are objectionable from either an operational or aesthetic point of view. Specifically, the invention is directed to the use of compositions comprising a combination of 1,3-dichloroacetone oxime acetate and beta-bromo-beta-nitrostyrene.

8 Claims, No Drawings

SLIME CONTROL COMPOSITIONS AND THEIR USE

This is a continuation-in-part of Ser. No. 545,676 filed Jan. 30, 1975, now abandoned.

BACKGROUND OF THE INVENTION

The formation of slime by microorganisms is a problem which attends many systems. For example, lagoons, lakes, ponds, pools, and such systems as cooling water systems and pulp and paper mill systems all possess conditions which are conductive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Furthermore, slime carried through the cooling system plugs and fouls lines, valves, strainers, etc. and deposits on heat exchange surfaces. In the latter case, the impedance of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Of greater significance, the slime becomes entrained in the paper produced to cause breakouts on the paper machines with consequent work stoppages and the loss of production time or unsightly blemishes in the final product which result in rejects and wasted output. The previously discussed problems have resulted in the extensive utilization of biocides in cooling water and pulp and paper mill systems. Materials which have enjoyed widespread use in such applications include chlorine, organo-mercurials, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the ability of chlorine to react which results in the expenditure of the chlorine before its full biocidal function may be achieved. Other biocides are attended by odor problems and hazards in respect to storage, use or handling which limit their utility. To date, no one compound or type of compound has achieved a clearly established predominance in respect to the applications discussed. Likewise, lagoons, ponds, lakes, and even pools, either used for pleasure purposes or used for industrial purposes for the disposal and storage of industrial wastes, become, during the warm weather, beseiged by slime due to microorganism growth and reproduction. In the case of the recreational areas, the problem of infection, etc. is obvious. In the case of industrial storage or disposal of industrial materials, the microorganisms cause additional problems which must be eliminated prior to the materials use or the waste is treated for disposal.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Instead, their effectiveness is rapidly reduced as the result of exposure to physical conditions such as temperature, association with ingredients contained by the system toward which they exhibit an affinity of substantivity, etc., with a resultant restriction or elimination or their biocidal effectiveness.

As a consequence, the use of such biocides involves their continuous or frequent addition to systems to be treated and their addition to a plurality of points or zones in the systems to be treated. Accordingly, the cost of the biocide and the labor cost of such means of applying it are considerable. In other instances, the difficulty of access to the zone in which slime formation is experienced precludes the effective use of a biocide. For example, in a particular system there is no access to an area at which slime formation occurs and it may only be applied at a point which is upstream in the flow system. However, the physical or chemical conditions, e.g., chemical reactivity, thermal degradation, etc. which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at a plurality of points, and even then a graduated biocidal effect will be experienced between one point of addition to the system and the next point downstream at which the biocides may be added. In addition to the increased cost of utilizing and maintaining plural feed points, gross ineconomies in respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

It is an object of the present invention to provide methods and compositions for controlling slime-forming microorganisms in aqueous systems such as cooling water systems and pulp and paper mill systems, and for controlling slime formation or microorganism populations in aqueous bodies in general. Moreover, another object of the invention is the provision of methods and compositions for controlling slime-forming microorganisms in any aqueous system which is conducive to the growth and reproduction of microorganisms and, in particular, cooling water and paper and pulp mill systems which employ a combination of 1,3-dichloroacetone oxime acetate and beta-bromo-beta-nitrostyrene.

In practice of the invention, the combination is added to the particular system being treated; for example, cooling water systems, paper and pulp mill systems, pools, ponds, lagoons, lakes, etc. in a quantity adequate to control the slime-forming microorganisms which are contained by, or which may become entrained in, the system which is treated. It has been found that such compositions and methods control the growth and occurrence of such microorganisms as may populate these particular systems.

1,3-dichloroacetone oxime acetate, as disclosed in U.S. Pat. No. 3,733,419, is available commercially as Stauffer R-22938. Beta-bromo-beta-nitrostyrene, as disclosed in U.S. Pat. No. 3,871,860, is available commercially from Givaudan Corporation as Giv-Guard BNS.

The inventive compositions are comprised of 1,3-dichloro-aacetone oxime acetate and beta-bromo-beta-nitrostyrene, either compound being present in such a quantity as to impart a synergistic behavior to the composition as a whole, the weight ratio of the Stauffer R-22938 to the Giv-Guard BNS ranging from about 95:5 to about 10:90. When these two ingredients are mixed, the resulting mixtures possess a high degree of slimicidal activity of the individual ingredients comprising the mixture. Accordingly, it is therefore possible to produce a more effective slime-control agent than has previously been available. Because of the enhanced activity of the mixture, the total quantity of the biocide required for an effective treatment may be reduced. In addition, the high degree of biocidal effectiveness which is provided by each of the ingredients may be exploited without use of the higher concentrations of each.

To demonstrate the synergism which is provided by the inventive combinations of compounds, the data as set forth in the Table below were developed.

EXAMPLE 1

Synergism was demonstrated, in separate experiments, by adding Compound A and Compound B in varying ratios and over a range of concentrations to liquid nutrient medium which was subsequently inoculated with a standard volume of a bacterial suspension. Following two days' incubation, the lowest concentration of each ratio which prevented growth of the bacteria was taken as the end point. Growth or no growth was determined by turbidity or clarity, respectively, in the medium. End points for the various mixtures were then compared with end points for the pure active ingredients working alone in concomitantly prepared culture bottles. Synergism was determined by the method described by F. C. Kull, P. C. Eisman, H. D. Sylwestrowicz and R. L. Mayer, APPLIED MICROBIOLOGY, 9, 538–41, (1961) and the relationship, $$\frac{Q_A}{Q_a} + \frac{Q_B}{Q_b} \begin{array}{l} <1 \text{ is synergism,} \\ =1 \text{ is additivity} \end{array} \quad >1 \text{ is antagonism,}$$

and where, $Q_a$ = Quantity of Compound A, acting alone, producing an end point $Q_b$ = Quantity of Compound B, acting alone, producing an end point $Q_A$ = Quantity of Compound A, in the mixture, producing an end point $Q_B$ = Quantity of Compound B, in the mixture, producing an end point For the mixtures of Compounds A and B, and for Compound A and B acting alone, the following results were observed.

Summary of synergistic activity of varying percentages of Compound A and Compound B:

SYNERGISTIC COMBINATION

Compound A: 1,3-dichloroacetone oxime acetate (Stauffer R-22938)

Compound B: beta-bromo-beta-nitrostyrene

TABLE I

EXPERIMENT I
TEST ORGANISM
AEROBACTER AEROGENES

| Weight ratio of A to B | Quantities Producing End Points (ppm) | | | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|
| | $Q_A$ | $Q_B$ | Mixture | | | |
| 100/0 | 16.0 | — | 16.0 | — | — | — |
| 95/5 | 8.55 | 0.45 | 9.0 | .53 | .08 | .61 |
| 50/50 | 3.75 | 3.75 | 7.5 | .23 | .62 | .85 |
| 0/100 | — | 6.0 | 6.0 | — | — | — |

TABLE II

EXPERIMENT II

| Weight Ratio Of A to B | Quantities Producing End Points (ppm) | | | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|
| | $Q_A$ | $Q_B$ | Mixture | | | |
| 100/0 | 12.0 | — | 12.0 | — | — | — |
| 30/70 | 1.35 | 3.15 | 4.5 | 0.11 | 0.39 | 0.50 |
| 20/80 | 0.9 | 3.60 | 4.5 | 0.08 | 0.45 | 0.53 |
| 10/90 | 0.5 | 4.5 | 5.0 | 0.04 | 0.56 | 0.60 |
| 0/100 | — | 8.0 | 8.0 | — | — | — |

The mode of establishing the synergistic behavior of the compositions of the present invention is a widely used and an industrially acceptable procedure. Although it is believed that the above is sufficient in explaining the procedure, for a further description thereof reference can be made to U.S. Pat. No. 3,231,509 and its file history where data of this nature was considered to be acceptable. Moreoever, the article by Kull et al published in APPLIED MICROBIOLOGY, 9, 538–541, will furnish additional information in this regard.

For the testing to ascertain synergistic behavior, *Aerobacter aerogenes* was favored since this microorganism is found to exist and found to be most troublesome in pulp and paper producing processes, as well as in cooling towers. Moreover, this microorganism is difficult to control and/or kill and accordingly its existence does give rise to troublesome slime. In view of the foregoing, it can then be appreciated that since *Aerobacter aerogenes* is prevalent in most slime-affected systems and since this microorganism is difficult to control or kill, that once control of this microorganism is maintained, then for all practical purposes the total microorganism population with its different types is considered controlled.

When the inventive compositions are employed in the treatment of cooling or paper mill water, they are preferably utilized in the form of relatively dilute solutions or dispersions. For example, a preferred solution comprises between 5% to 65% by weight of the synergistic combination in admixture with various solvents and solubilizing agents.

Surfactants such as the alkylaryl polyether alcohols, polyether alcohols, alkyl benzene sulfonates and sulfates, and the like, may also be employed to enhance the dispersibility and stability of these formulations. The foregoing solutions of the biocidal compositions are utilized in order to insure the rapid and uniform dispersibility of the biocides within the industrial water which is treated. It has been found that either aqueous or non-aqueous solvents are generally suitable in the preparation of compositions of the invention. For example, organic solvents such as methyl cellosolve and aliphatic and aromatic hydrocarbons, e.g., kerosene, can be used quite successfully. Based upon the synergism study as outlined above, it was ascertained that in the treatment of paper mill and cooling water, effective biocidal action is obtained when the concentration or treatment level of the combination or admixture of biocides is between 0.5 parts per million to 1000 parts per million, and preferably between 1 and 100 parts per million, based upon the total content of the system treated, such as the total quantity of cooling water or paper mill water.

The compositions may also be utilized for the preservation of slurries and emulsions containing carbohydrates, proteins, fats, oils, etc. Dosage levels for this purpose range in the vicinity of 0.01% to 5%.

The compositions of the invention which can be prepared by merely combining the respective ingredients and mixing thoroughly at standard conditions may be fed continuously to the treated system, e.g., by means of a metered pump, or may be fed periodically at intervals calculated to control the growth of slime-forming organisms in the system. Naturally, in the treatment of cooling water the feeding of the inventive compositions must be designed to compensate for blow-down in those systems which employ that expedient.

As would be expected, the inventive composition may be added to the cooling water or paper and pulp mill systems at any convenient point. Naturally, in once-through or non-circulating systems, the composition must be added upstream from the point or points at which microorganism control is desired. In circulating systems or pulp and paper systems, the compositions may be added at any point provided that the time lapse and the conditions experienced between point of addition and the point at which the effect of the composition is experienced are not so drastic as to result in the neutralization of the effect of the composition.

SLIME CONTROL EFFECTIVENESS

The inventive methods and materials were tested with respect to their performance in the control of slime formation in industrial systems. In this test an industrial recirculating water was obtained from a system which was currently experiencing problems in respect to the formation of slime by microorganisms. Such tests do not demonstrate the efficiency of the biocide employed with respect to specific species of microorganiams, but instead supply a practical demonstration of the efficacy of the biocide tested in relation to those communities of microorganisms which have evidenced their ability to form slime in actual industrial systems.

In testing of recirculating water samples, a substrate evaluation was employed. In such testing, identical portions of water samples are treated with varying concentrations of biocide and two portions are left untreated to serve as controls. The control portions are plated for total count at the beginning of biocide treatment and all portions are plated for total count at some suitable time period(s) after beginning biocide treatment. Using the counts obtained from the platings, the percentage kill (based on the initial control count) may be calculated In the following example, the water sample was taken from a cooling tower located in northeastern Pennsylvania.

For the purposes of comparison, a composition of this invention was evaluated with two recognized commercial biocides.

TABLE III

| Biocidal Material | Quantity of Biocide(ppm) | Percent Kill After 3 Hours |
| --- | --- | --- |
| Stauffer R-22938 (5%) | 5 | +10 |
| | 10 | 22 |
| Beta-bromo-beta-nitrostyrene(5%) | 25 | 40 |
| | 50 | 65 |
| Inert (90%) | 100 | 80 |
| Pentachlorophenol (10% Active) | 5 | 1 |
| | 10 | 73 |
| | 25 | 98 |
| | 50 | 99 |
| | 100 | 99 |
| Sodium dimethyldithiocarbamate (10% Active) | 5 | +8 |
| | 10 | 15 |
| | 25 | 47 |
| | 50 | 60 |
| | 100 | 65 |

EFFICACY RELATIVE TO FUNGI

In order to ascertain whether in fact the inventive compositions were effective in controlling fungi, evaluations were made following the procedure described by Shema et al, "JOURNAL FOR THE TECHNICAL ASSOCIATION OF THE PULP AND PAPER INDUSTRY", 36, 20A–30A, 1953. The described procedure generally entails incorporating the biocide under test in a nutrient substrate such as agar, malt, etc. and pouring the resulting medium in a Petri dish and allowing the medium to solidify. A button of fungus inoculum is placed on the surface of the solidified medium and the medium is incubated for a period of 14 days. After the period, the diameter of the colony is measured and compared with the diameter of the button of inoculum originally placed upon the surface. If there is no increase in the diameter, the growth of the fungus is considered to be completely inhibited and the treatment level which effectuates this is considered the inhibitory concentration.

The fungi species utilized as the test microorganism to evaluate the efficacy of the present compositions were *Penicillium expansum* and *Aspergillus niger*. The study revealed that the above 10% active composition of this invention inhibited the growth of *Penicillium expansum* at a treatment level of 400 ppm and 600 ppm completely inhibited the growth of *Aspergillus niger*.

BACTERICIDAL EFFECTIVENESS

The bactericidal effectiveness of a 1/1 mixture of the two components of this invention (10% Active) is demonstrated by the following data in which the inhibiting power is shown in comparison with a commercial biocide. *Aerobacter aerogenes* was employed as the test organism and a substrate technique was utilized. Specifically, the biocidal mixture was added in gradually increasing quantities to nutrient agar media which was then innoculated with *Aerobacter aerogenes*. The preparation was then incubated for 48 hours. The below values indicate the quantity of biocide required to achieve complete inhibition of the growth of the test organism. The biocide RX-38 is available commercially from Betz Laboratories, Inc. and contains as active ingredients about 5% methylene bisthiocyanate and about 17% hexachloro dimethyl sulfone by weight.

| Biocide Materials | Inhibition quantity (ppm) |
|---|---|
| 1. Stauffer R-22938 (5%) beta-bromo-beta-nitrostyrene (5%) Inert (90%) | 60 |
| 2. Betz Slime-Trol RX-38 (100%) | 30 |

Accordingly, since the waters of pulp and paper mills and the water of cooling water systems generally predominately contain bacteria such as *Aerobacter aerogenes* and some fungi such as *Penicillium expansum* and *Aspergillus niger*, it is apparent from the foregoing evaluations and studies that the inventive composition will effectuate the claimed objective of controlling microorganisms of aqueous systems.

It should be noted that while the preponderance of evidence has been derived from the treatment of samples taken from paper and pulp mill aqueous systems, the compositions and methods of the present invention are broadly applicable to the treatment of aesthetic waters as well as industrial waters such as cooling waters which are plagued by deposits formed by slime-forming organisms, or by the very presence of such organisms.

Having thus described the invention, what is claimed is:

1. A composition for the control of the microorganism Aerobacter aerogenes in aqueous systems comprising a mixture of 1,3-dichloroacetone oxime acetate, with beta-bromo-beta-nitrostyrene wherein the weight ratio of the acetate to the nitrostyrene ranges from about 95:5 to about 10:90 respectively.

2. The composition of claim 1 wherein said ratio is about 50:50.

3. A method for controlling the growth of the microorganism Aerobacter aerogenes in an aqueous system which comprises adding to said system a growth inhibiting amount of a composition comprised of a mixture of 1,3-dichloroacetone oxime acetate with beta-bromo-beta nitrostyrene wherein the weight ratio of the acetate to the nitrostyrene ranges from about 95:5 to about 10:90 respectively.

4. The method of claim 3 wherein said ratio is about 50:50.

5. The method of claim 3 wherein said composition is added to said system in an amount of from 0.1 to about 1000 parts per weight of said composition per million parts by weight of said aqueous system.

6. The method of claim 5 wherein said composition amount is from about 1 to about 100 parts per million of said aqueous system.

7. The method of claim 5 wherein the aqueous system is that of a cooling water system.

8. The method of claim 5 wherein the aqueous system is that of a pulp and paper mill system.

* * * * *